United States Patent
Shammai et al.

(10) Patent No.: US 7,210,343 B2
(45) Date of Patent: May 1, 2007

(54) METHOD AND APPARATUS FOR OBTAINING A MICRO SAMPLE DOWNHOLE

(75) Inventors: Michael Shammai, Houston, TX (US); Robert Gordon, The Woodlands, TX (US); Francisco Galvan Sanchez, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/836,996

(22) Filed: Apr. 30, 2004

(65) Prior Publication Data

US 2004/0244971 A1 Dec. 9, 2004

Related U.S. Application Data

(60) Provisional application No. 60/467,668, filed on May 2, 2003.

(51) Int. Cl.
*G01N 23/00* (2006.01)
*E21B 49/08* (2006.01)

(52) U.S. Cl. .................. 73/152.28; 73/152.14; 73/152.23

(58) Field of Classification Search .......... 73/152.28, 73/152.24, 152.46, 152.55, 152.14, 152.23; 250/253, 255; 166/256, 250.1
See application file for complete search history.

(56) References Cited

U.S. PATENT DOCUMENTS

| | | | |
|---|---|---|---|
| 3,448,611 A | 6/1969 | Lebourg | 73/152.28 |
| 3,611,799 A | 10/1971 | Davis | 73/152.24 |
| 4,936,139 A | 6/1990 | Zimmerman et al. | 73/152.26 |
| 5,178,178 A * | 1/1993 | Hartl | 137/114 |
| 5,859,430 A | 1/1999 | Mullins et al. | 250/255 |
| 5,934,374 A * | 8/1999 | Hrametz et al. | 166/264 |
| 6,092,416 A | 7/2000 | Halford et al. | 73/152.23 |
| 6,688,390 B2 | 2/2004 | Bolze et al. | 166/264 |
| 2002/0060067 A1 | 5/2002 | Bolze et al. | 166/264 |
| 2002/0194906 A1 | 12/2002 | Goodwin et al. | 73/152.46 |
| 2003/0033866 A1 | 2/2003 | Diakonov et al. | 73/152.55 |
| 2003/0209066 A1 | 11/2003 | Goodwin | 73/152.05 |
| 2004/0104341 A1 | 6/2004 | Betancourt et al. | 250/255 |
| 2004/0216521 A1 | 11/2004 | Shammai et al. | 73/152.55 |

FOREIGN PATENT DOCUMENTS

| | | |
|---|---|---|
| EP | 0 295 923 A | 12/1988 |
| EP | 1 205 630 A | 5/2002 |

* cited by examiner

*Primary Examiner*—Hezron Williams
*Assistant Examiner*—Tamiko Bellamy
(74) *Attorney, Agent, or Firm*—Madan, Mossman & Sriram, P.C.

(57) ABSTRACT

The present invention provides a downhole sample tank and a plurality of micro sample chambers. The micro sample chambers can have at least one window for introduction of visible, near-infrared (NIR), mid-infrared (MIR) and other electromagnetic energy into the tank for samples collected in the micro sample chamber downhole from an earth boring or well bore. The window is made of sapphire or another material capable of allowing electromagnetic energy to pass through the window. The entire micro sample chamber can be made of sapphire or another material capable of allowing electromagnetic energy to pass another material enabling visual inspection or analysis of the sample inside the micro sample chamber. The micro sample chamber enables immediate testing of the sample on location at the surface to determine the quality of the sample in the main sample tank or to enable comprehensive testing of the sample.

30 Claims, 6 Drawing Sheets

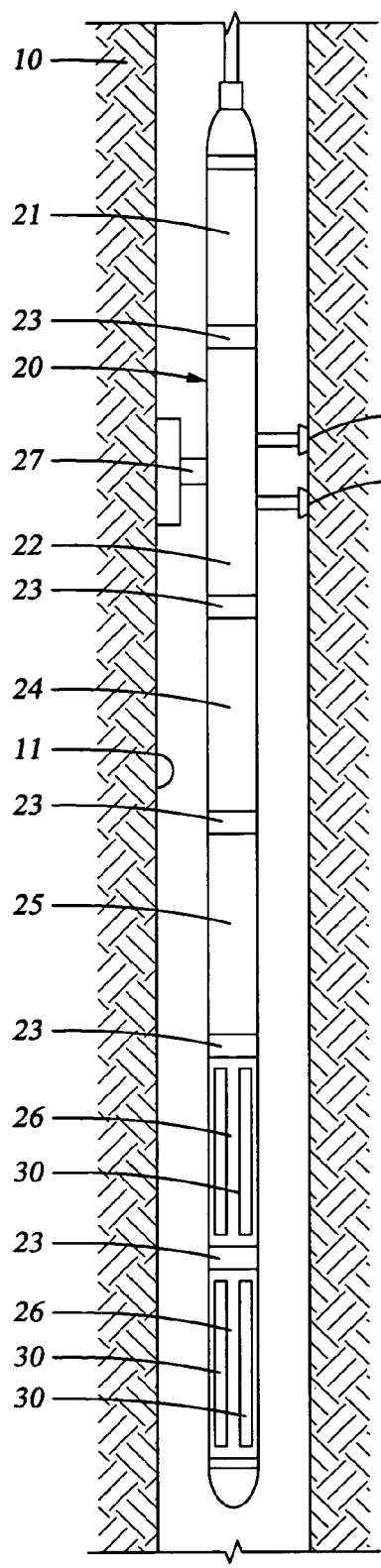
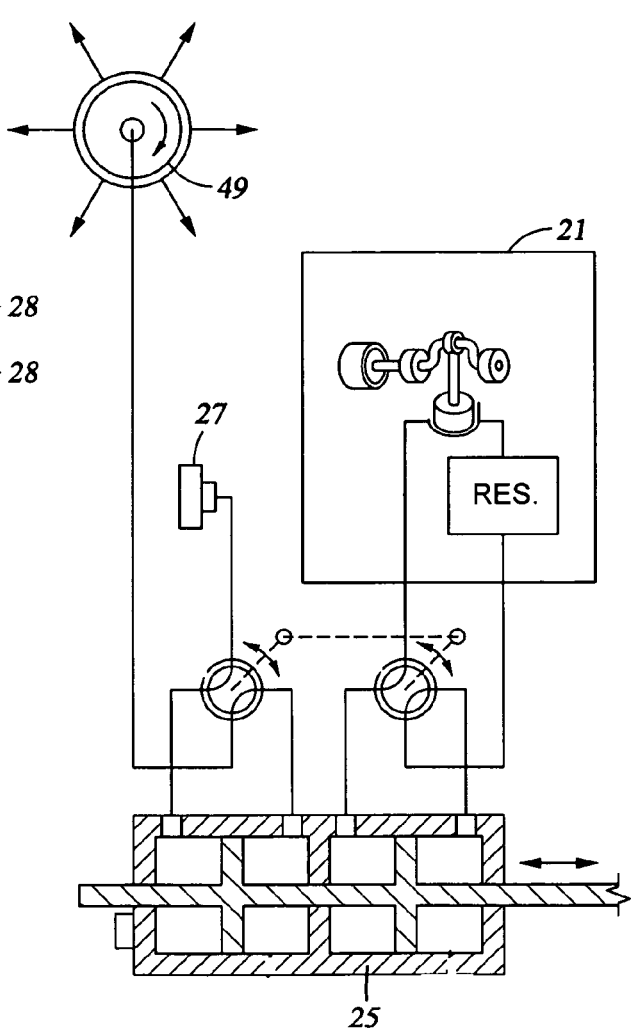
Fig. 3
Fig. 2

METHOD AND APPARATUS FOR OBTAINING A MICRO SAMPLE DOWNHOLE

CROSS REFERENCE TO RELATED APPLICATIONS

This patent application claims priority from U.S. Provisional Patent Application Ser. No. 60/467,668 entitled "A Method and Apparatus for an Advanced Optical Cylinder" by M. Shammai et al. filed on May 2, 2003.

BACKGROUND OF THE INVENTION

1. Field of the Invention

The present invention relates generally to the field of downhole sampling analysis and in particular to obtaining an aliquot formation fluid micro sample down hole for rapid analysis on location to determine the quality of the down hole sample.

2. Summary of the Related Art

Earth formation fluids in a hydrocarbon producing well typically comprise a mixture of oil, gas, and water. The pressure, temperature and volume of formation fluids control the phase relation of these constituents. In a subsurface formation, high well fluid pressures often entrain gas within the oil above the bubble point pressure. When the pressure is reduced, the entrained or dissolved gaseous compounds separate from the liquid phase sample. The accurate measurement of pressure, temperature, and formation fluid composition from a particular well affects the commercial viability for producing fluids available from the well. The data also provides information regarding procedures for maximizing the completion and production of the respective hydrocarbon reservoir.

Certain techniques analyze the well fluids downhole in the well bore. U.S. Pat. No. 6,467,544 to Brown, et al. describes a sample chamber having a slidably disposed piston to define a sample cavity on one side of the piston and a buffer cavity on the other side of the piston. U.S. Pat. No. 5,361,839 to Griffith et al. (1993) disclosed a transducer for generating an output representative of fluid sample characteristics downhole in a wellbore. U.S. Pat. No. 5,329,811 to Schultz et al. (I 994) disclosed an apparatus and method for assessing pressure and volume data for a downhole well fluid sample.

Other techniques capture a well fluid sample for retrieval to the surface. U.S. Pat. No. 4,583,595 to Czenichow et al. (1986) disclosed a piston actuated mechanism for capturing a well fluid sample. U.S. Pat. No. 4,721,157 to Berzin (1988) disclosed a shifting valve sleeve for capturing a well fluid sample in a chamber. U.S. Pat. No. 4,766,955 to Petermann (1988) disclosed a piston engaged with a control valve for capturing a well fluid sample, and U.S. Pat. No. 4,903,765 to Zunkel (1990) disclosed a time-delayed well fluid sampler. U.S. Pat. No. 5,009,100 to Gruber et al. (1991) disclosed a wireline sampler for collecting a well fluid sample from a selected wellbore depth. U.S. Pat. No. 5,240,072 to Schultz et al. (1993) disclosed a multiple sample annulus pressure responsive sampler for permitting well fluid sample collection at different time and depth intervals, and U.S. Pat. No. 5,322,120 to Be et al. (1994) disclosed an electrically actuated hydraulic system for collecting well fluid samples deep in a wellbore.

Temperatures downhole in a deep wellbore often exceed 300 degrees F. When a hot formation fluid sample is retrieved to the surface at 70 degrees F, the resulting drop in temperature causes the formation fluid sample to contract. If the volume of the sample is unchanged, such contraction substantially reduces the sample pressure. A pressure drop causes changes in the situ formation fluid parameters, and can permit phase separation between liquids and gases entrained within the formation fluid sample. Phase separation significantly changes the formation fluid characteristics, and reduces the ability to evaluate the actual properties of the formation fluid.

To overcome this limitation, various techniques have been developed to maintain pressure of the formation fluid sample. U.S. Pat. No. 5,337,822 to Massie et al. (1994) pressurized a formation fluid sample with a hydraulically driven piston powered by a high-pressure gas. Similarly, U.S. Pat. No. 5,662,166 to Shammai (1997) used a pressurized gas to charge the formation fluid sample. U.S. Pat. Nos. 5,303,775 (1994) and 5,377,755 (1995) to Michaels et al. disclosed a bi-directional, positive displacement pump for increasing the formation fluid sample pressure above the bubble point so that subsequent cooling did not reduce the fluid pressure below the bubble point.

Typically, sample tanks are transported to laboratories for analysis for determination of formation fluid properties based on the sample. The samples typically have to be transferred to a transportation tank, thus risking sample damage and spoilage due to pressure loss and formation of bubbles or asphaltene precipitation within the sample. Moreover, even if the sample is transferred successfully to the laboratory, it typically takes weeks or months to receive a full laboratory analysis of the sample. Thus there is a need for a rapid sample analysis system that provides accurate results and eliminates the risk of sample spoilage.

SUMMARY OF THE INVENTION

The present invention addresses the shortcomings of the related art described above. The present invention provides a downhole sample tank and a plurality of micro sample chambers. The micro sample chambers can have at least one window for introduction of visible, near-infrared (NIR), mid-infrared (MIR) and other electromagnetic energy into the tank for samples collected in the micro sample chamber downhole from an earth boring or well bore. The window is made of sapphire or another material capable of allowing electromagnetic energy to pass through the window. The entire micro sample chamber can be made of sapphire or another material capable of allowing electromagnetic energy to pass another material enabling visual inspection or analysis of the sample inside the micro sample chamber. The micro sample chamber enables immediate testing of the sample on location at the surface to determine the quality of the sample in the main sample tank or to enable comprehensive testing of the sample.

The sample tank and micro sample chambers filled by pumping formation fluid against a piston biased against hydrostatic pressure. The sample tank and micro sample chambers are over pressurized by pumping or a gas charge to raise the sample pressure to a pressure above the bubble point pressure for the sample to prevent adverse pressure drop. The micro sample chambers can be removed at the surface for immediate testing via optical analysis of the sample intact inside of the micro sample chamber or by affixing the micro sample chamber to test block for pumping the sample from the micro sample chamber into the test block for gas chromatography testing. A biasing water pressure charge can be applied to the micro sample to further ensure that the micro sample remains above the bubble point pressure. The viscosity of the sample inside of the micro sample tank can be determined by weighing the micro sample tank empty and again after it is filled with the sample to determine the weight of the sample inside the known volume of the micro sample chamber.

BRIEF DESCRIPTION OF THE FIGURES

For detailed understanding of the present invention, references should be made to the following detailed description of the exemplary embodiment, taken in conjunction with the accompanying drawings, in which like elements have been given like numerals, wherein:

FIG. 2 is a schematic of the invention in operative assembly with cooperatively supporting tools;

FIG. 3 is a schematic of a representative formation fluid extraction and delivery system;

DETAILED DESCRIPTION OF AN EXEMPLARY EMBODIMENT

Figure 1:
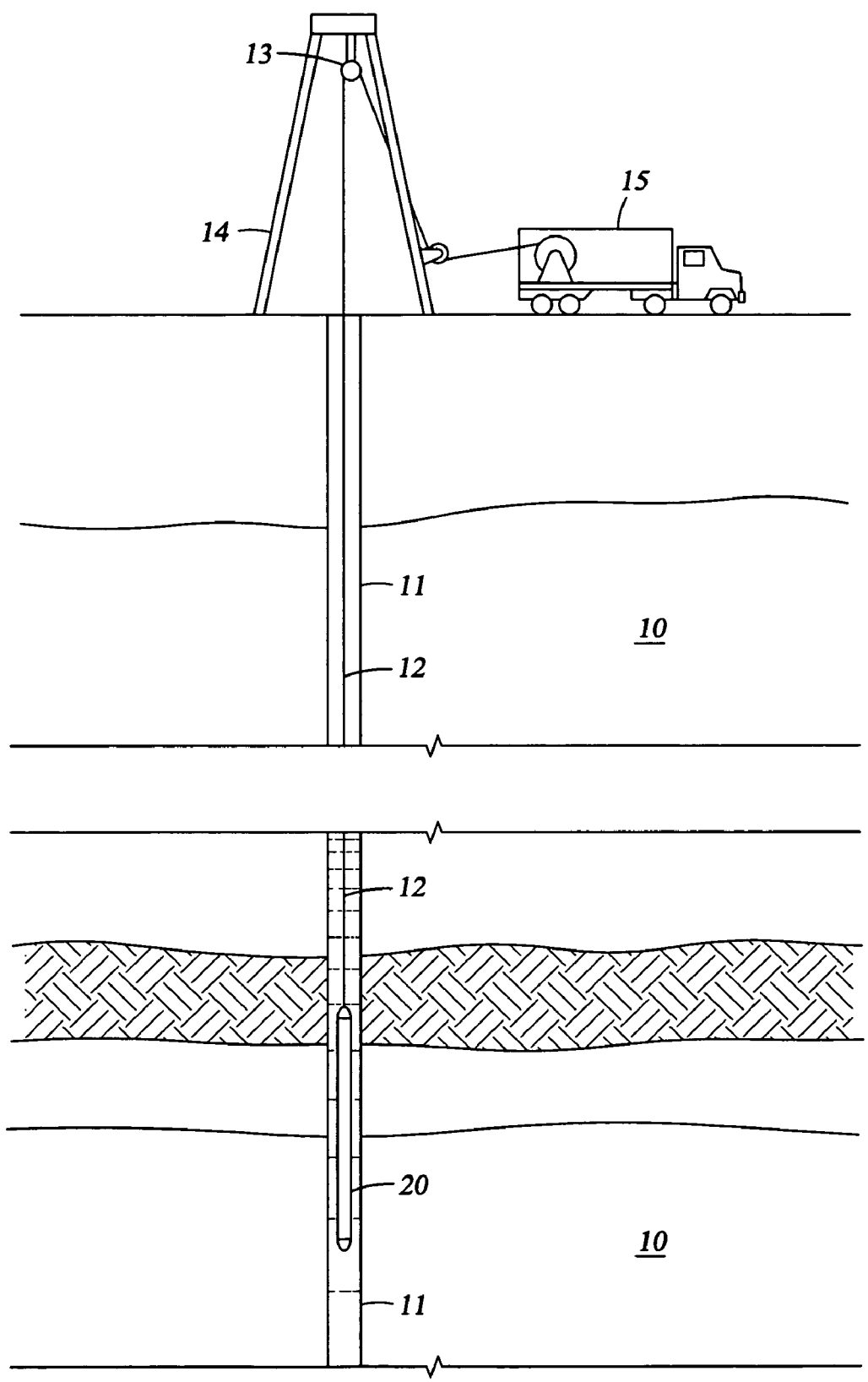
FIG. 1 is a schematic earth section illustrating the invention operating environment.

FIG. 1 schematically represents a cross-section of earth 10 along the length of a wellbore penetration 11. Usually, the wellbore will be at least partially filled with a mixture of liquids including water, drilling fluid, and formation fluids that are indigenous to the earth formations penetrated by the wellbore. Hereinafter, such fluid mixtures are referred to as "wellbore fluids". The term "formation fluid" hereinafter refers to a specific formation fluid exclusive of any substantial mixture or contamination by fluids not naturally present in the specific formation.

Suspended within the wellbore 11 at the bottom end of a wireline 12 is a formation fluid sampling tool 20. The wireline 12 is often carried over a pulley 13 supported by a derrick 14. Wireline deployment and retrieval is performed by a powered winch carried by a service truck 15, for example.

Pursuant to the present invention, an exemplary embodiment of a sampling tool 20 is schematically illustrated by FIG. 2. In the present example, the sampling tools comprise a serial assembly of several tool segments that are joined end-to-end by the threaded sleeves of mutual compression unions 23. An assembly of tool segments appropriate for the present invention may include a hydraulic power unit 21 and a formation fluid extractor 23. Below the extractor 23, a large displacement volume motor/pump unit 24 is provided for line purging. Below the large volume pump is a similar motor/pump unit 25 having a smaller displacement volume that is quantitatively monitored as described more expansively with respect to FIG. 3. Ordinarily, one or more sample tank magazine sections 26 are assembled below the small volume pump. Each magazine section 26 may have three or more fluid sample tanks 30.

The formation fluid extractor 22 comprises an extensible suction probe 27 that is opposed by bore wall feet 28. Both, the suction probe 27 and the opposing feet 28 are hydraulically extensible to firmly engage the wellbore walls. Construction and operational details of the fluid extraction tool 22 are more expansively described by U.S. Pat. No. 5,303,775, the specification of which is incorporated herewith.

Figure 4:
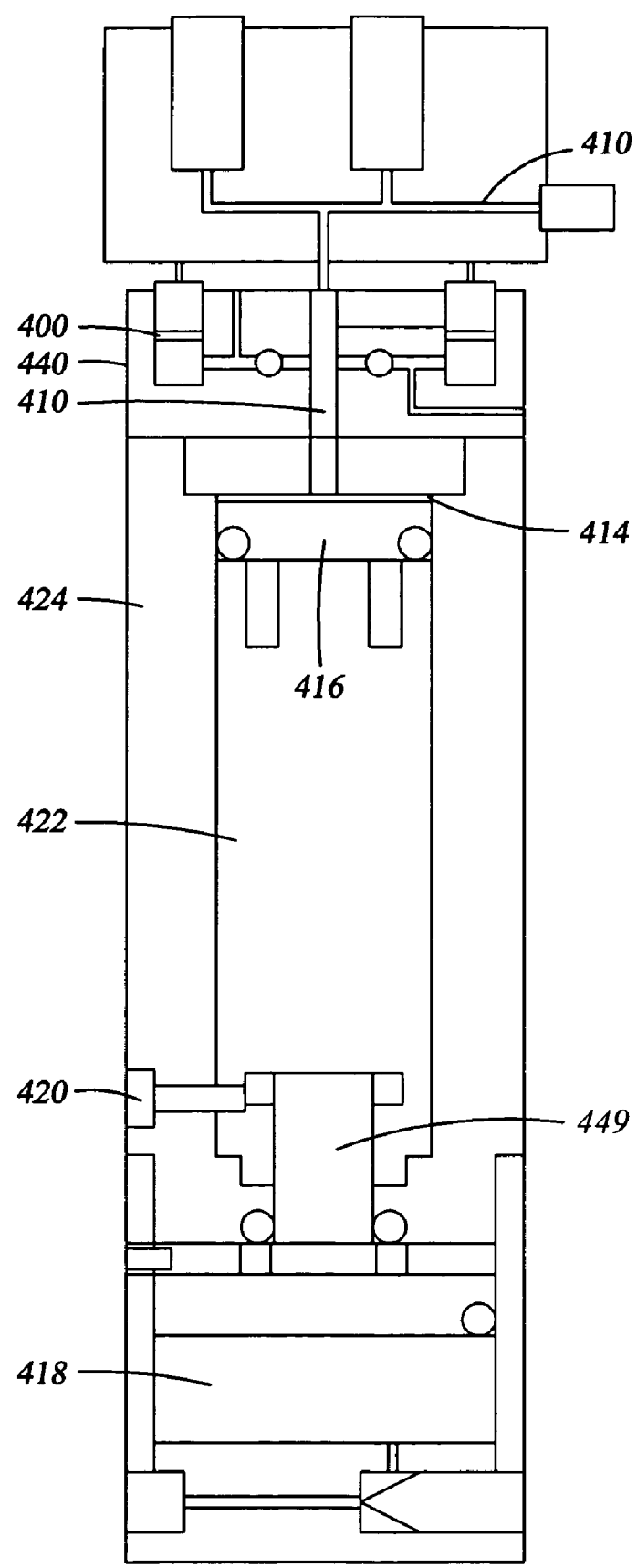
FIG. 4 is an illustration of an exemplary micro sample chamber.

Turning now to FIG. 4, the mains sample chamber 414 is in fluid communication with the micro sample 510 chamber through flow line 410. Sample input 412 receive formation fluid from pump 25. Piston 416 is biased with hydrostatic pressure via orifice 420 which is open to the borehole. Thus, sample fluid from the formation is pumped into the main sample chamber and the micro sample chambers 510 against hydrostatic pressure from the wellbore. As more fluid is pumped into the sample chamber 414, the volume of sample chamber 414 expands, as does the volume of micro sample chambers 510. A nitrogen bias is also supplied in chamber 418 which applies pressure to the back side of piston 416 once piston travels down to abut connecting rod 449. The nitrogen gas charge applies pressure to the sample contained in main sample chamber 414 and micro sample chambers 510.

Hydrostatic chamber 422 applies hydrostatic pressure underneath piston 416 which keeps the sample fluid being pumped into main sample chamber and micro sample chambers above hydrostatic pressure. The micro sample assemblies 400 are housed in tool body 440 from which the micro sample assemblies 400 can be removed for inspection and testing of the sample inside of micro sample chamber 510.

Figure 5:
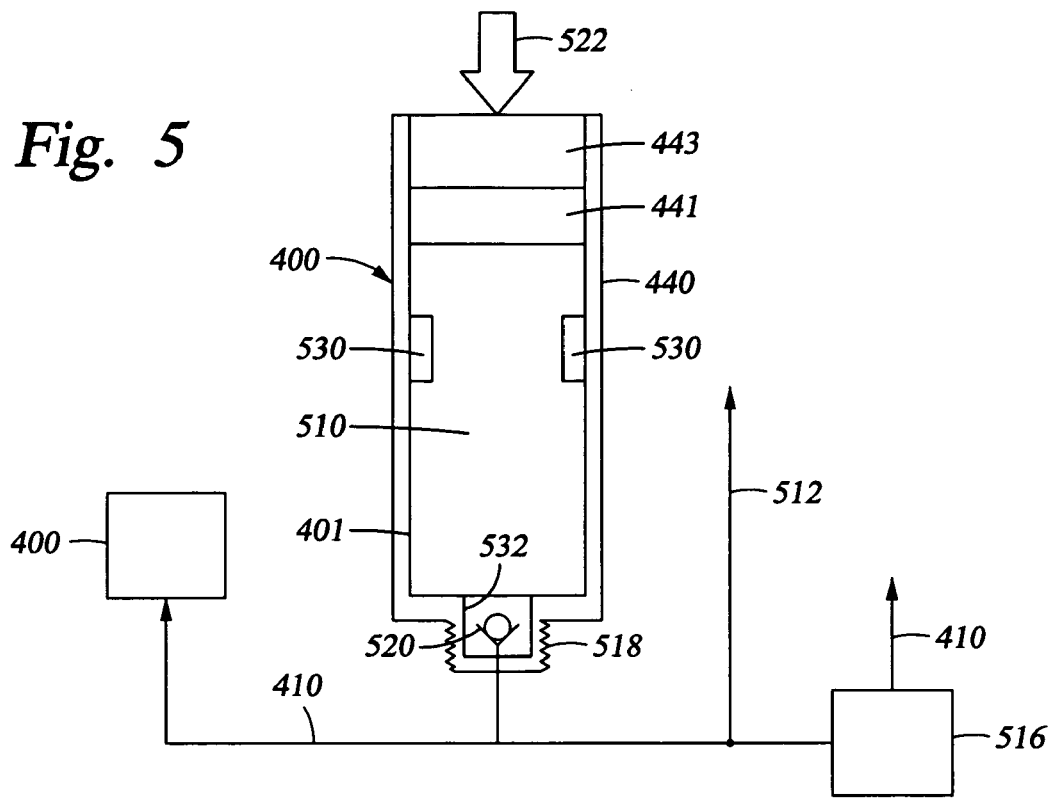
FIG. 5 is a more detailed illustration of the micro sample chambers of FIG. 4 with a check valve and a purge line.

Turning now to FIG. 5, a more detailed illustration of the micro sample assembly 400 is shown. A valve 516 is open to provide fluid communication between the main sample chamber 414 and the micro sample chambers 510. The micro sample chambers 510 are provided with biasing pistons 441 which are open to the bore hole hydrostatic pressure via orifice 522. Thus, the formation fluid is pumped into sample flow line 410 and is opposed by hydrostatic pressure by pistons 441 in the micro sample chambers 510 and piston 416 in the main sample chamber 414.

The micro sample assembly 400 is weighed before a run while it is empty and weighed again after being filled with sample fluid to determine the weight of the sample fluid. Knowing the volume of the micro sample chamber 510, a density for the fluid sample inside for the micro sample chamber 510 is determined by dividing the weight (mass) by the volume. The sample fluid density can be used to determine fluid viscosity.

Flow line 410 enable formation fluid to enter micro sample chamber 510 via check valve 520. Check valve 520 allows formation fluid to enter into the sample chamber but does not allow fluid to exit unless the check valve is opened with a pin 612 as shown in FIG. 6.

Valve 516 is closed after the sample fills micro sample chambers 510 and main sample chamber 414 so that pistons 441 and 416 respectively have bottomed out to expand the respective sample chambers to maximum volume. Once valve 516 is closed, purge line 512 is opened to relieve the pressure in flow line 410 between valve 516 and check valve 520. Relieving this pressure enables removal of micro sample assembly 400 by unscrewing the assembly threads 532 from tool body threads 518, so that the sample inside of the micro sample assembly 400 contained in micro sample chamber 510 can be visually inspected and analyzed.

Micro sample assembly 400 can be made of metal with windows made of a material such as sapphire the enables visual inspection and optical analysis of the contents of the micro sample chamber. The entire micro sample assembly 400 or chamber walls 401 surrounding micro sample chamber 510 can be made of a material such as sapphire the enables visual inspection and optical analysis of the contents of the micro sample chamber.

Figure 6:
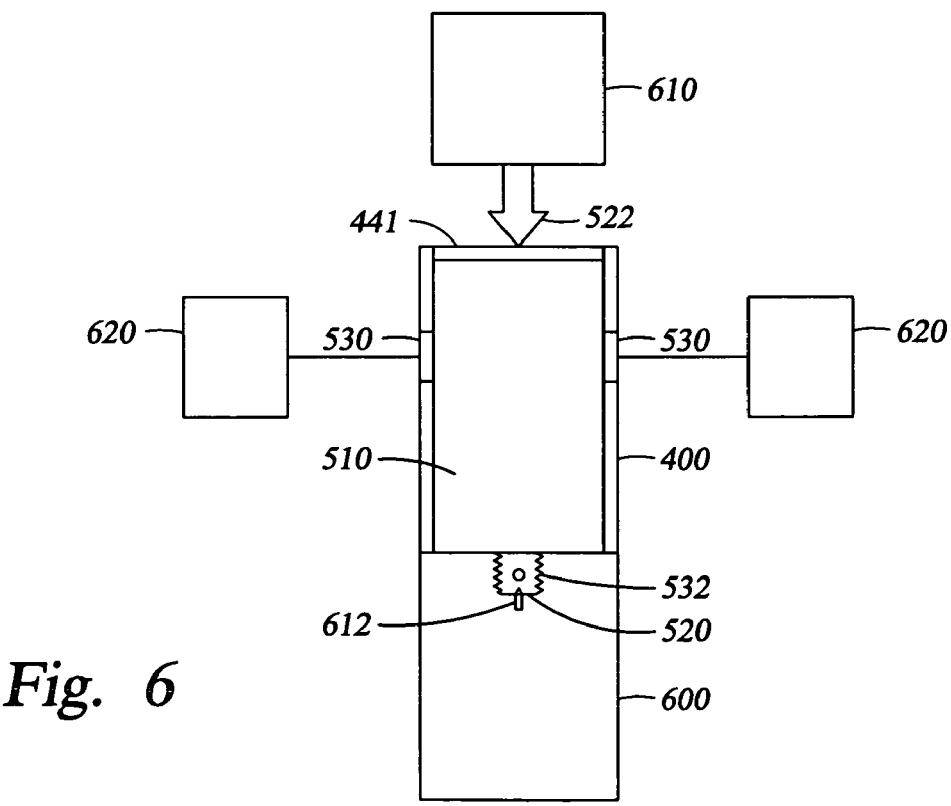
FIG. 6 illustrates the micro sample assembly disconnected from the down hole tool and undergoing analysis of the micros sample.

Turning now to FIG. 6, a water pump can be connected to orifice 522 to apply pressure to the back side of micro sample assembly piston 441 to pressurize sample in sample chamber 510 during transfer of the micro sample into a test apparatus, such as a gas chromatograph 600. The micro sample assembly screws into the test block 600 and pin 612 engages check valve 520 to allow the sample inside of sample chamber 510 to enter test block 600. The water pressure from pump 610 keeps the sample under pressure to prevent flashing of the sample inside of the sample chamber 510 during transfer to the test block.

The present example of the micro sample chamber provides one or more optical conduits, which in this example are high-pressure sapphire windows 530 for ingress and egress of electromagnetic energy into the micro sample chamber 510 for optical analysis of parameters of interest for formation fluid sample 510. The entire micro sample chamber can be made of sapphire or another material which enables electromagnetic energy to pass through the material, thereby enabling visual inspection and noninvasive spectral and other analysis of the contents of the micro sample chamber. Optical conduits other than a sapphire window are acceptable.

In surface operations, as shown in FIG. 6, the micro sample assembly is removed from a sample tank carrier. An external optical analyzer 620 comprising an NIR/MIR ultraviolet or visible light source and spectrometers provided for surface non-invasive analysis. The optical analyzer 620 is comprises a NIR/MIR light source a and a NIR/MIR light sensor for analysis of light transmittance, fluorescence and total attenuated reflectance. That is, without disturbing the fluid sample or requiring transferring the sample to another Department of Transportation (DOT) approved chamber for transport to an off-site laboratory for analysis.

The external optical analyzer 620 in the current example uses wavelength ranges from 1500 nm to 2000 nm to scan the fluid sample to determine or estimate through soft modeling techniques, parameters of interest, such as sample contamination percentage, gas oil ratio (GOR), density and asphaltene deposition pressure. A tunable diode laser and a Raman spectrometer are also provided in analysis module 620 for spectral analysis of the fluid sample. Each of the light sources and sensors are located inside of the micro sample chamber 510 or communicate with the interior of the micro sample chamber via the optical window 530 or an equivalent optical conduit providing data or electromagnetic energy ingress and egress to the interior of the sample tank and the sample retained therein.

Figure 7:
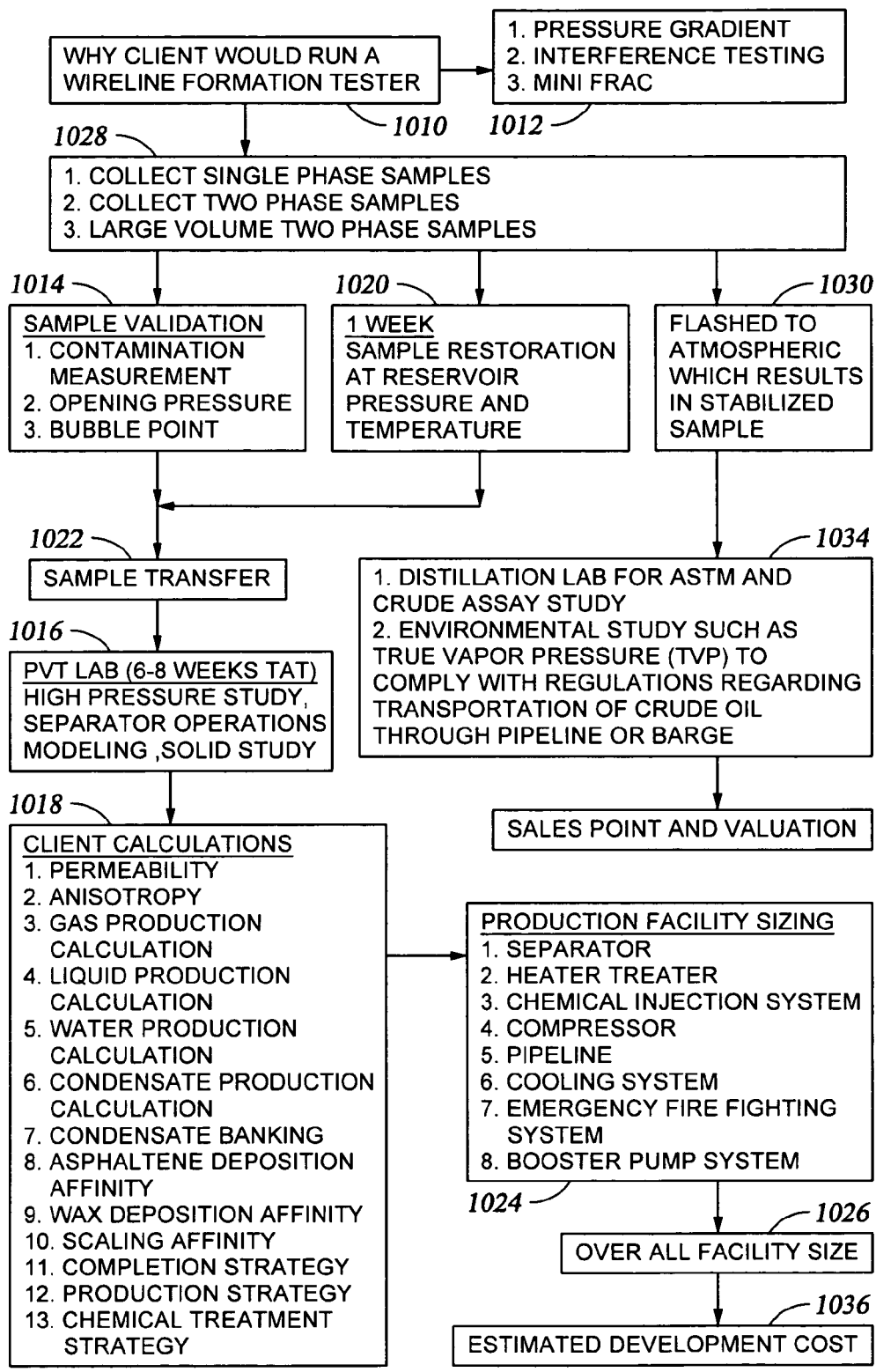
FIG. 7 is an illustration of a common known analysis procedure.
Figure 8:
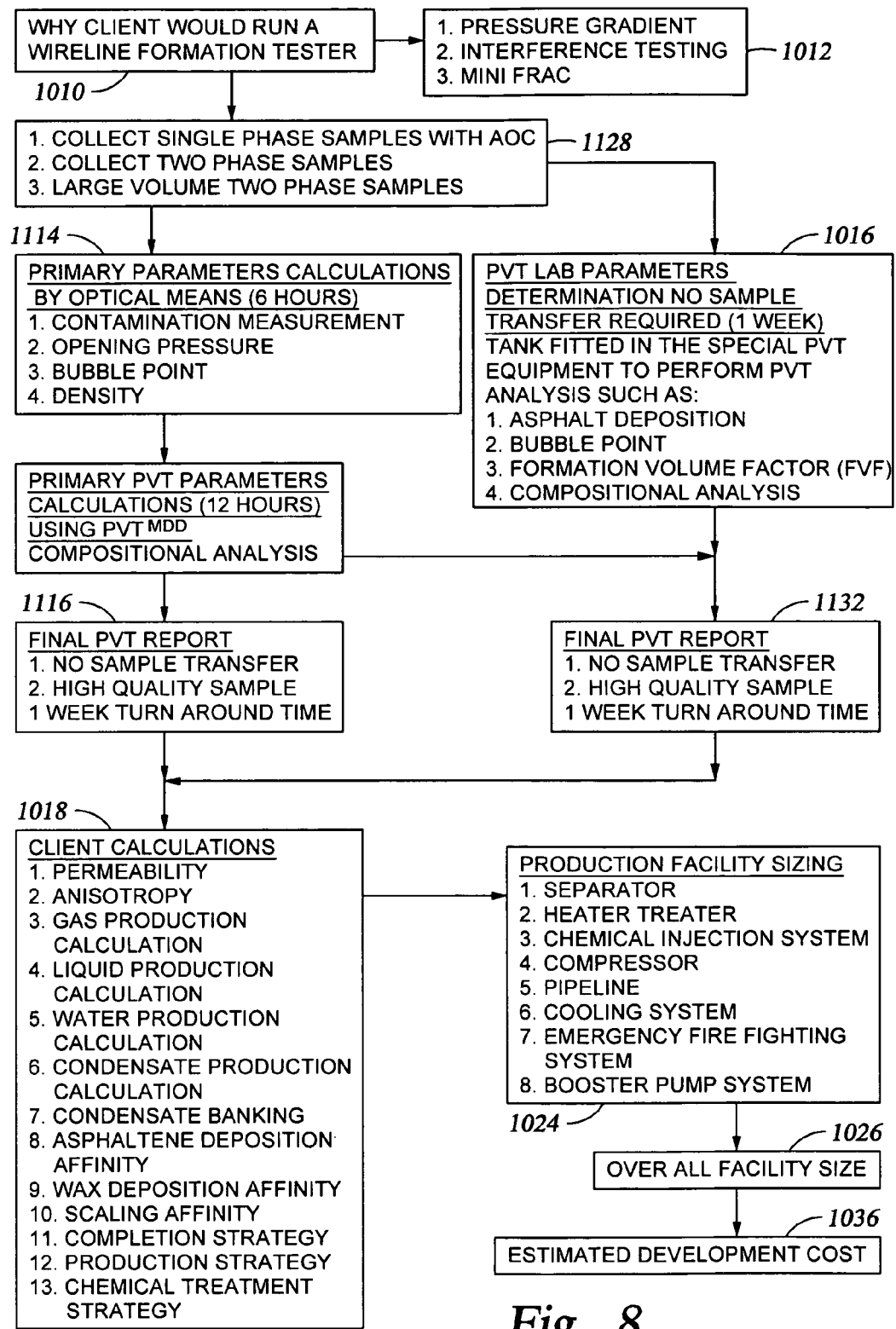
FIG. 8 is an illustration of the new improved procedure provided by the present invention.

Some of the numerous advantages of the present invention are shown by comparison to FIG. 7, a prior art system and FIG. 8, the new method and apparatus design provided by the AOA of the present invention. Note that in FIG. 8 that a primary parameter calculation by optical techniques 1114 is available immediately or in less than six hours and a final PVT report 1132 in less than a week or less rather than six to eight weeks as shown in FIG. 7 for the prior art system. An advantage for the disclosed method and apparatus is that no sample transfer is required, as non-invasive surface or down hole equipment in external equipment 620 perform PVT and spectral analysis to determine asphaltene deposition, bubble point, formation volume factor, compositional analysis and additional analysis described herein.

In another embodiment, the method and apparatus of the present invention is implemented as a set computer executable of instructions on a computer readable medium, comprising ROM, RAM, CD-ROM, Flash RAM or any other computer readable medium, now known or unknown that when executed cause a computer to implement the functions of the present invention.

While the foregoing disclosure is directed to the exemplary embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto:

The invention claimed is:

1. A downhole tool for determining a parameter of interest of a fluid sample comprising:
   a main sample chamber; and
   a micro sample chamber wherein micro sample chamber, the main sample chamber and the fluid sample are in fluid communication downhole and wherein the main sample chamber contains a first portion of the fluid sample and the micro sample chamber contains second portion of the fluid sample, wherein the micro sample chamber is removable from the main sample chamber for determining the parameter of interest for the second portion of the fluid in the micro sample chamber to determine the parameter of interest for the first portion of the fluid sample in the main sample chamber; and
   an analyzer associated with the micro sample chamber for analyzing the fluid sample downhole.

2. The apparatus of claim 1, wherein the micro sample chamber has a known weight and volume for determining density of the fluid.

3. The apparatus of claim 1, wherein the entire micro sample chamber is made of a material that allows passage of electromagnetic energy for analysis of the sample in the micro sample chamber.

4. The apparatus of claim 1, further comprising:
   a pressure charge for maintaining a pressure on the fluid in the micro sample chamber sample during egress of the tool from the well bore.

5. The apparatus of claim 1, further comprising:
   wherein the analyzer comprises at least one of the set consisting of a tunable diode laser, an infrared light source and infrared sensor, and a Raman spectrometer for analyzing the fluid sample.

6. The apparatus of claim 5, further comprising:
   a micro sample chamber piston for opposing the fluid from a sample pump during filling of the micro sample chamber with the fluid sample.

7. The apparatus of claim 1, further comprising:
   a water pressure charge for pressurizing the sample in the micro sample chamber after egress from down hole.

8. The apparatus of claim 1, further comprising:
   a check valve that admits fluid into the micro sample chamber and prevents the fluid from exiting the micro sample chamber, the check valve being removed with the micro sample chamber.

9. The apparatus of claim 8, further comprising:
   a valve for isolating the micro sample chamber from the main sample chamber.

10. The apparatus of claim 9, further comprising:
    a purge line for relieving pressure between the micro sample chamber and the main sample chamber.

11. The apparatus of claim 1, wherein substantially the entire micro sample chamber is made of a material to enable visual inspection of the sample inside of the micro sample chamber.

12. The apparatus of claim 1, wherein the micro sample chamber is made of a material to enable optical analysis of the sample inside of the micro sample chamber.

13. The apparatus of claim 1, wherein the micro sample chamber is removable from the tool for analysis of the sample at the surface by external analysis equipment.

14. The apparatus of claim 1, wherein the micro sample chamber is removable from the micro sample chamber for analysis of the micro sample fluid sample at a surface.

15. A method for determining a parameter of interest for a fluid sample comprising:
   filling a main sample chamber and a micro sample chamber in fluid communication with the fluid sample, thereby containing a first portion of the fluid sample in a main sample chamber and containing a second portion of the formation fluid sample in a micro sample chamber in fluid communication with the main sample chamber downhole;
   removing the micro sample chamber from the main sample chamber; and
   analyzing the second portion of the fluid sample in the micro sample chamber with an analyzer associated with the micro sample chamber to determine a parameter of interest for the first portion of the fluid sample in the main sample chamber.

16. The method of claim 15, wherein analyzing the second portion of the fluid further comprises:
   weighing the micro sample chamber containing the second portion of the fluid sample;
   determining the weight of the second portion of the fluid in the micro sample chamber from the weight of the micro sample containing the second portion of the fluid minus a weight of the micro sample chamber when empty; and determining at least one of the set consisting of density and viscosity of the fluid from the weight of the fluid and the volume of the sample chamber containing the fluid.

17. The method of claim 15, wherein substantially the entire micro sample chamber is made of a material that allows passage of electromagnetic energy for analysis of the sample in the micro sample chamber.

18. The method of claim 15, further comprising:
   maintaining a pressure on the second portion of the fluid in the micro sample chamber sample with a pressure charge during egress of the tool from the well bore.

19. The method of claim 15, further comprising:
   applying a hydrostatic pressure bias acting on a sample inside of the micro sample chamber.

20. The method of claim 15, further comprising:
   opposing a sample pump during filling of the micro sample chamber with the second portion of the fluid sample.

21. The method of claim 15, further comprising:
   pressurizing the sample in the micro sample chamber after egress from down hole.

22. The method of claim 15, further comprising:
   admitting fluid into the micro sample chamber and preventing fluid from exiting the micro sample chamber with a check valve, the check valve being removed with the micro sample chamber.

23. The method of claim 15, further comprising:
   a valve for isolating the micro sample chamber from the main sample chamber.

24. The method of claim 23, further comprising:
   relieving pressure between the micro sample chamber and the main sample chamber.

25. The method of claim 15, further comprising:
   visually inspecting the fluid sample inside of the micro sample chamber.

26. The method of claim 15, further comprising:
   optically analyzing the second portion of the fluid sample inside of the micro sample chamber.

27. The method of claim 15, further comprising:
   removing the micro sample chamber from the tool; and
   analyzing the second portion of the fluid sample inside of the micro sample chamber at the surface by external analysis equipment to determine the quality of the first portion of the fluid sample inside of the main chamber.

28. The method of claim 15, further comprising:
   removing the micro sample chamber for analysis of the second portion of the fluid sample at the surface by external analysis equipment to determine a parameter of interest for the first portion of the fluid sample inside of the main chamber.

29. A down hole tool for determining a parameter of interest for a fluid sample comprising:
   a main sample chamber inside of the tool for containing a first portion of the fluid sample; and
   a micro sample chamber in fluid communication with and removable from the main sample chamber and the fluid sample downhole for containing a second portion of the formation fluid sample and an analyzer associated with the micro sample chamber for analyzing the fluid sample.

30. A downhole tool for determining a parameter of interest for a fluid sample comprising:
   (a) a main sample chamber inside of the tool receiving a first portion of the fluid sample; and
   (b) a micro sample chamber in fluid communication with the main sample chamber receiving a second portion of the fluid sample at substantially the same time the main sample chamber receives the first portion of the fluid sample, wherein:
      (i) the micro sample chamber is removable from the main sample chamber; and
      (ii) the second portion of the fluid sample can be removed from the micro sample chamber without disturbing the first fluid portion in the main sample chamber; and
   (c) an analyzer associated with the micro sample chamber for analyzing the fluid sample.

* * * * *